United States Patent [19]
Uskokovic et al.

[11] 4,376,207
[45] Mar. 8, 1983

[54] CHIRAL SYNTHESIS OF AMINO SUGARS

[75] Inventors: Milan R. Uskokovic, Upper Montclair; Peter M. Wovkulich, Nutley, both of N.J.

[73] Assignee: Hoffmann-La Roche Inc., Nutley, N.J.

[21] Appl. No.: 326,731

[22] Filed: Dec. 2, 1981

Related U.S. Application Data

[62] Division of Ser. No. 179,126, Aug. 18, 1980, Pat. No. 4,324,726, which is a division of Ser. No. 60,261, Jul. 25, 1979, Pat. No. 4,252,964.

[51] Int. Cl.³ .......................................... C07D 309/02
[52] U.S. Cl. ..................................... 549/417; 560/172
[58] Field of Search ................... 260/345.8 R, 340.3, 260/340.5 R; 549/417

[56] References Cited

U.S. PATENT DOCUMENTS 4,024,333  5/1977  Horton et al. .................... 536/17 R

FOREIGN PATENT DOCUMENTS 2752115  6/1978  Fed. Rep. of Germany .... 536/17 R

OTHER PUBLICATIONS

Badoche et al., Chem. Abstract, 39, 1853-5, (1945).

Primary Examiner—Nicky Chan
Attorney, Agent, or Firm—Jon S. Saxe; George M. Gould; William H. Epstein

[57] ABSTRACT

A simple and economic chiral synthesis of optically active methyl L-acosaminide and methyl L-daunosaminide from propenyl acetate, said methyl L-acosaminide and methyl L-daunosaminide being coupling agents for the production of known antitumor agents.

4 Claims, No Drawings

CHIRAL SYNTHESIS OF AMINO SUGARS

This application is a divisional application of Ser. No. 06/179,126 filed Aug. 18, 1980, now U.S. Pat. No. 4,324,726 issued July 13, 1982, which in turn is a divisional application of Ser. No. 06/060,261 filed July 25, 1979, now U.S. Pat. No. 4,252,964 issued Feb. 24, 1981.

BACKGROUND OF INVENTION

The amino sugar methyl L-daunosaminide, i.e. the compound of the formula

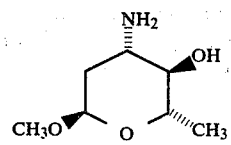   I-A is a known coupling agent with the antibiotic daunomycinone or adriamycinone to produce the natural antibiotics daunomycin and adriamycin respectively. See Arcamone et al. J. of Med. Chem., 1975, Vol. 18, No. 7, page 703 and Arcamone et al., Cancer Chemotherapy Rep., 6, 123 (1975). In accordance with the aforementioned Arcamone et al. articles, methyl L-acosaminide which has the formula:

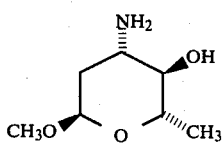   I-B is converted to C4′epi—daunomycin and C4′epi—adriamycin, known antitumor agents, by forming a derivative of the compound of formula I-B, i.e. a compound of the formula

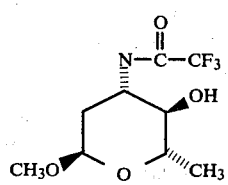   II via the procedure described by Fuchs, J. Antibiotics, 32, 223 (1979).

SUMMARY OF INVENTION

In accordance with this invention, there has been found a new synthetic approach to producing the compound of formula I-A and I-B via an intermediate of the formula

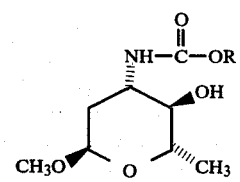   III wherein R is lower alkyl or racemic or enantiomeric mixtures thereof.

The compound of formula III is synthesized in a simple and economic manner starting with the reaction of propenyl acetate which has the formula:

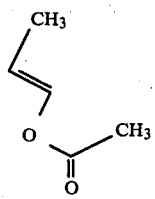   IV and a compound of the formula

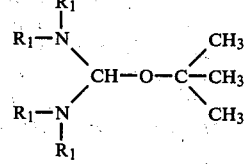   V wherein $R_1$ is alkyl, aryl or aralkyl to produce a compound of the formula

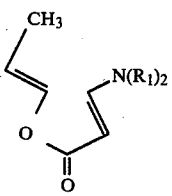   VI wherein $R_1$ is as above.

DETAILED DESCRIPTION

As used herein, lower alkyl connotes straight or branched chain saturated aliphatic hydrocarbon groups containing 1 to 7 carbon atoms (e.g. methyl, ethyl, n-propyl, isopropyl and hexyl). Lower alkoxy means alkoxy groups having from 1 to 7 carbon atoms (e.g. methoxy, ethoxy and isopropoxy). Lower alkylene denotes alkylene groups of from 2 to 6 carbon atoms such as ethylene, propylene and butylene. Lower alkanol connotes alkanols having 1–7 carbon atoms such as methanol, propanol and hexanol. Lower alkanoic acid connotes lower alkyl carboxylic acids such as acetic acid, isopropionic acid and hexanoic acid.

Aryl denotes mononuclear aromatic hydrocarbon groups such as phenyl and the like which can be unsubstituted or substituted in one or more positions with halogen, nitrogen, lower alkylenedioxy, lower alkyl or lower alkoxy. Aryl also denotes polynuclear aryl groups such as napthyl, anthryl, phenanthryl, azulyl and the like which can be unsubstituted or substituted with one or more of the aforementioned substituents.

Aralkyl connotes a group comprising an aryl moiety as defined hereinbefore, particularly benzyl and lower alkyl substituted benzyls (e.g. cumyl). Halogen denotes all forms of halogen such as fluorine, chlorine, bromine and iodine. Alkali metals include lithium, sodium potassium and rubidium. Alkaline earth metals include barium, magnesium, calcium and strontium.

In the pictorial representations of the compounds of this application, a solid tapering line (⊪—) indicates a substituent which is in the β-orientation (above the plane of the molecule) and a dashed line (≡) indicates a substituent which is in the α-orientation (below the plane of the molecule) and a wavy line (∼∼) indicates a substituent which is either in the α or β position or is a mixture of compounds containing these substituents in the α or β position.

In the first step of the synthesis of this invention, the compound of formula IV is reacted with a compound of formula V to produce the compound of formula VI. In this reaction, the compound of formula V is simply added to the compound of formula IV. In carrying out this reaction, temperature and pressure are not critical and this reaction can be carried out at room temperature and atmospheric pressure. On the other hand, elevated or reduced temperatures can be utilized. Generally, it is preferred to carry out this reaction at the boiling point or reflux temperature of the reaction mixture. However, any temperature of from 0° C. to 100° C. can be utilized. While it is preferred to carry out this reaction without the necessity of utilizing an inert organic solvent, any conventional inert organic solvent can be utilized, if desired.

In accordance with this invention, the compound of formula VI is converted to the compound of formula III via the following reaction scheme:

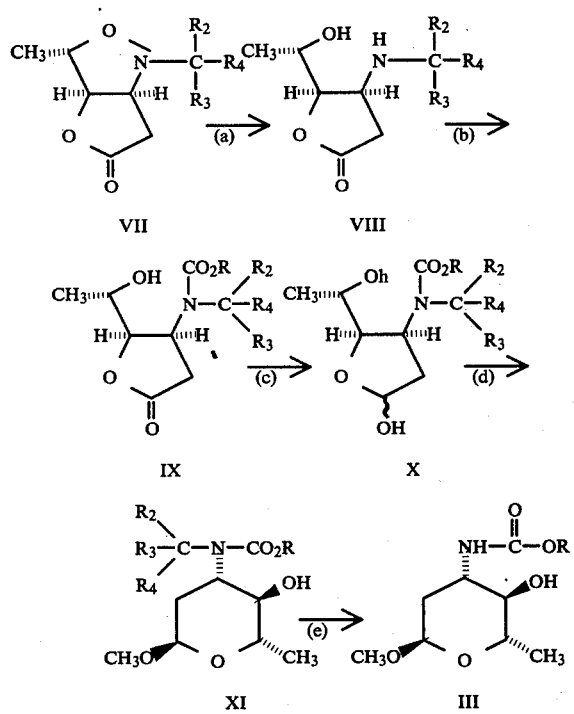

wherein R is as above, $R_2$ and $R_4$ are hydrogen, aryl, aralkyl, or lower alkyl; and $R_3$ is aryl; or racemic or enantiomeric mixtures of these compounds.

In the first step of this synthesis, the compound of formula VI is reacted with a hydroxylamine of the formula:

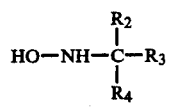
XII wherein $R_2$, $R_3$ and $R_4$ are above or acid addition salts thereof. Where the compound of formula XII is optically inactive, the compound of formula VII is produced as a racemic mixture. On the other hand where the S-form of the compound of formula XII where $R_4$ is hydrogen and $R_2$ is other than other hydrogen and $R_3$, i.e. a compound of the formula:

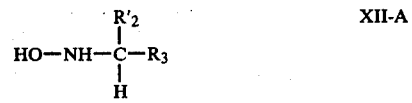
XII-A wherein $R_2'$ is lower alkyl, aryl or aralkyl and $R_3$ is as above and where $R_2'$ is other than $R_3$ then the reaction produces the enantiomer represented by formula VII. Furthermore, where the compound of formula XII-A is utilized as a mixture of enantiomers such as 80% S by weight and 20% by weight R, rather than as pure S, the enantiomer of formula VII will be produced with an optical purity of 80% by weight in admixture about 20% of its other enantiomer. This enantiomeric mixture can be carried out throughout the reaction or can be separated by conventional means. A preferred compound of formula XII-A is where $R_3$ is aryl particularly the S-enantiomer.

If the compound of formula VII is formed as the single enantiomer represented, the optical configuration is carried out through the rest of the reaction sequence so that the compounds of formula I-A and I-B are produced having the optical configuration hereinbefore designated. On the other hand, if the compound of formula VII is formed as a racemate, this racemic mixture is carried out throughout the entire synthesis until this racemate is resolved to produce the desired specific enantiomeric configuration.

In carrying out the reaction to produce the compound of formula VII, the compound of formula VI is reacted with the compound of formula XII or an acid addition salt thereof. Any conventional acid addition salt of formula XII can be utilized. Among the acids which form the acid addition salts of the compound of formula XII are included the inorganic acids such as sulfuric, hydrochloric and hydrobromic acids, as well as the organic acids such as oxalic acid, malic acid, acetic acid, etc.

The compound of formula VI is converted to the compound of formula VII by reacting the compound of formula VI with the compound of formula XII. This reaction is carried out in an inert organic solvent. Any conventional inert organic solvent can be utilized to carry out this reaction. Among the preferred inert organic solvents are the aromatic hydrocarbon solvents such as benzene, xylene, toluene, etc. In carrying out this reaction, temperature and pressure are not critical and this reaction can be carried out at room temperature and atmospheric pressure. Generally this reaction is carried out at a temperature of from 20° C. to 150° C. with the reflux temperature of the reaction mixture being preferred.

The compound of formula VII is converted to the compound of formula VIII by treating the compound of formula VII with a reducing agent selected from the group consisting of zinc in acetic acid or an alkali metal borohydride. Any of the conditions conventional in reducing with zinc in acetic acid or with an alkali metal borohydride can be utilized in carrying out this reaction. Among the preferred alkali metal borohydrides is sodium borohydride.

The compound of formula VIII is converted to the compound of formula IX by reacting the compound of formula VIII with a haloformate of the formula

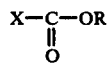

wherein X is halogen and R is as above. Any of the conditions conventional in reacting an amine with a haloformate can be utilized in carrying out this reaction. Generally, it is preferred to carry out this reaction in an inert organic solvent. Any conventional inert organic solvent can be utilized. Among the preferred inert organic solvents are included tetrahydrofuran. In carrying out this reaction, temperature and pressure are not critical and this reaction can be carried out at room temperature and atmospheric pressure.

The compound of formula IX is converted to the compound of formula X by treating the compound of formula X with a reducing agent. Any conventional reducing agent which will reduce an ester to an aldehyde can be utilized in carrying out this reaction. Among the preferred reducing agents for carrying out this reaction are the alkyl aluminum hydride reducing agents such as diisobutyl aluminum hydride. Any of the conditions conventionally utilized in reducing with this reducing agent can be utilized in converting the compound of formula IX to the compound of formula X.

The compound of formula X is converted to the compound of formula XI via reaction step (d), by treating the compound of formula X with methanol in the presence of an acid catalyst. Any conventional acid catalyst can be utilized in carrying out this reaction. Among the preferred acid catalysts are included the cationic ion exchange resins. Among the preferred cationic ion exchange resins are included the aromatic sulfonic acid cationic ion exchange resins such as the polystyrene sulfonic type resins under tradename such as Amberlite IR-120, Dowex 50 and Amberlite CG 120 (Rohm and Haas). While the cationic ion exchange resins are preferred, any conventional acid catalyst such as an inorganic acid or organic acid can be utilized. Among the preferred acid catalysts are included sulfuric acid, hydrochloric acid, hydrobromic acid, acetic acid, p-toluenesulfonic acid, etc. In carrying out this reaction, there is no need to utilize an inert organic solvent. In fact, it is generally preferred to carry out this reaction in the presence of excess methanol. On the other hand, if desired, an inert organic solvent such as the solvents mentioned hereinbefore can be utilized in carrying out this reaction. Among the preferred inert organic solvents are the solvents mentioned before.

In carrying out the reaction of step (d), temperature and pressure are not critical and this reaction can be carried out at room temperature and atmospheric pressure. On the other hand, elevated or reduced temperature can be utilized. If desired, temperatures of from $-10°$ C. to $100°$ C. can be utilized with reflux temperatures being especially preferred.

The compound of formula XI can be converted to the compound of formula III by hydrogenolysis. Any conventional method of hydrogenolysis can be utilized to effect this conversion. Among the preferred methods is by treating the compound of formula XI with sodium in liquid ammonia. On the other hand, catalytic hydrogenation can be utilized as the hydrogenolysis procedure.

Any conventional method of catalytic hydrogenation can be utilized in carrying out this reaction.

The compound of formula III can be converted to the compound of formula I-B by basic hydrolysis. Any conventional method of basic hydrolysis such as by treating the compound of formula III with an alkali metal hydroxide or an alkaline earth metal hydroxide can be utilized. This reaction is usually carried out in an aqueous medium at reflux temperatures.

On the other hand, the compound of formula III can be converted to the compound of formula I-A via the following intermediates:

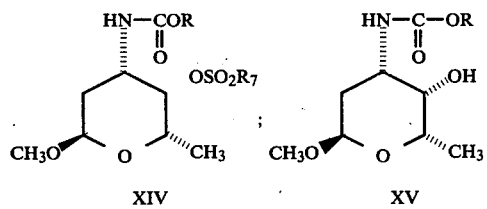

wherein R is as above and $R_7$ is lower alkyl or aryl or racemic or enantiomeric mixtures thereof.

The compound of formula III is converted to the compound of formula XIV by treating the compound of formula III with a lower alkyl sulfonyl halide or an aryl sulfonyl halide. Any of the conventional lower alkyl sulfonyl halides or aryl sulfonyl halides used as leaving groups can be utilized in effecting this conversion. Among the preferred alkyl or aryl sulfonyl halides are included methanesulfonyl chloride and toluenesulfonyl chloride. Any conventional method reacting a hydroxy with a sulfonyl halide leaving agent can be utilized for carrying out this reaction.

The compound of formula XIV is converted to the compound of formula XV by treating the compound of formula XIV with a mixture of a dimethylformamide and water. In carrying out this reaction, temperature and pressure are not critical and this reaction can be carried out at room temperature or atmospheric pressure. On the other hand, elevated or reduced pressures and temperatures can be utilized in carrying out this reaction. Generally, it is preferred to carry out this reaction at the reflux temperature of the reaction mixture. Generally, it is preferred to carry out this reaction in the presence of a buffering agent. Among the preferred buffering agents are the alkali metal salts of lower alkanoic acids such as sodium acetate.

The compound of formula XV is converted to the compound of formula I-A by basic hydrolysis in the same manner as described in connection with the conversion of the compound of formula III to the compound of formula I-B.

If the compound of formula VII is produced in its racemic form, the intermediates following in this reaction will also be in their racemic form. However, these intermediates in their racemic form can be resolved into the desired enantiomeric form during the reaction sequence. This can be accomplished through the intermediate of formula I-A, I-B, III, VIII, IX, XI and XV via the free hydroxy group contained therein. These compounds can be esterified with dicarboxylic acid such as succinic acid and the free carboxylic acid resulting therefrom treated with a optically active amine to form the diastereomeric salts. Typically optically active amine include arginine, brucine, alpha-methyl benzyl-amine, quinine and dehydroabietylamine. The resulting diastereomeric salts can be separated by conventional means such as crystallization or chromatography. After separation of the desired diastereomeric salt, the salt containing the desired enantiomeric configuration can be converted back to the free hydroxy compound by conventional means such as hydrolysis.

The compound of formula I-B can be converted to the known coupling agent for producing C4'-daunomycin or C4'-adriamycin, i.e. the compound of formula II via the following intermediate:

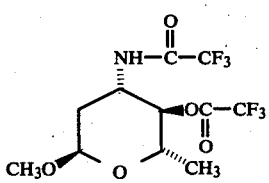   XIX

The compound of formula I-B is converted to the compound of formula XIX by reacting the compound of formula I-B with an anhydride of the formula:

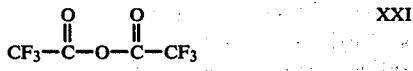   XXI

This reaction is carried out in an inert organic solvent preferably an ether solvent such as diethyl ether, tetrahydrofuran, etc. In carrying out this reaction, temperatures of from 0° C. to the reflux temperature of the reaction mixture can be utilized.

The compound of formula XIX is converted to the compound of formula II by treatment with methanol. In carrying out this reaction, the methanol acts as the solvent medium for the compound of formula XIX. In carrying out this reaction, temperature and pressure are not critical and the reaction can be carried out at room temperature and atmospheric pressure. Generally, temperatures of from 0° to 50° C. are utilized in this reaction.

In accordance with another embodiment of this invention, the compound of formula VII is converted to the compound of formula II via the following intermediates:

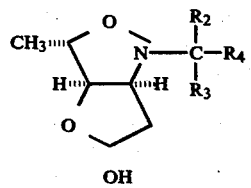   XXII

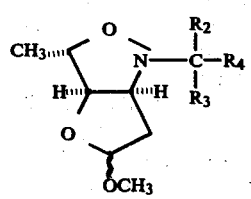   XXIII

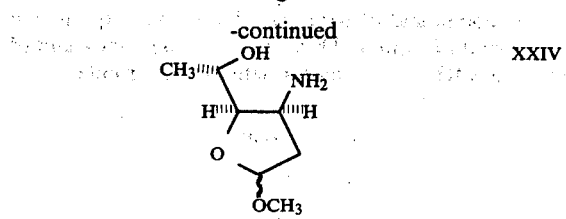

wherein $R_2$ and $R_3$ are as above or racemic or enantiomeric mixtures thereof.

The compound of formula VII is converted to the compound of formula XXII by reduction with analkyl aluminum hydride in the same manner as described in connection with the reduction of a compound of the formula IX to a compound of formula X hereinbefore. The compound of the formula XXII is converted to the compound of the formula XXIII by treating with methanol in the presence of a acid catalyst utilizing the same conditions described hereinbefore in connection with the conversion of a compound of the formula X to a compound of the formula XI.

The compound of formula XXIII is converted to the compound of formula XXIV by reducing the compound of formula XXIII by hydrogenolysis. The same conditions utilized in converting the compound of formula XI to the compound of formula III can be utilized in effecting this conversion.

The compound of formula XXIV is converted to the compound of formula I-C by treatment with methanol in the presence of an acid catalyst. The same condition described in connection with the conversion of a compound of the formula X to a compound of the formula XI can be utilized in effecting this conversion. The compound of formula I-C is converted to the compound of formula XIX-A by reacting the compound of formula I-C with the compound of formula XXI. This reaction is carried out in the same manner as described in connection with the conversion of the compound of formula I-B to the compound of formula XIX. The compound of formula XIX-A is converted to the compound of formula II-A by treating the compound of formula XIX-A with methanol in the manner described hereinbefore in connection with the conversion of the compound of formula XIX to the compound of formula II.

The compound of formula II can be formed from the compound II-A by separation of the two anomers which constitute the compound of formula II-A. This separation is accomplished by conventional means such as chromatography. On the other hand where the racemate of formula VII is utilized in the conversion of the compound of formula VII to the compound of formula II via the intermediates of the formula XXII, XXIII, XXIV, I-C, XIX-A, II-A, these racemates may be resolved into the desired enantiomer illustrated above through the free hydroxy group on the compounds of formula XXII, XXIV, I-C and II-A. The resolution through this hydroxy group into the enantiomer can take place utilizing this procedure described hereinbefore.

The invention is further illustrated by the following examples which are illustrative but not limitative of the claimed invention.

EXAMPLE 1 trans-3-(Dimethylamino)-2-propenoic acid, trans-propenyl ester

A solution of 20.0 g (0.2 mole) of trans-propenyl acetate and 101.0 g (0.6 mole) of bis(dimethylamino)-tert.-butoxymethane under argon was heated at 50° C. overnight (16½ hours). The excess reagent was removed by vacuum distillation (0.7 mmHg, oil bath at 50° C.). The residue was chromatographed rapidly on 300 g of silica gel 60 eluting with ethyl acetate/hexane (2:3 parts by volume) to give 28.2 g (91%) of trans-3-(dimethylamino)-2-propenoic acid, trans-propenyl ester which was used in the next step with no further purification. This material was sublimed (to remove yellow color) at 40°–50° C. 0.2 mmHg. The analytical sample was recrystallized from pentane. Mp 48°–48.5° C.

EXAMPLE 2

[3S[1(S*)-3β,3aβ,6aβ]]-Tetrahydro-3-methyl-1-(1-phenylethyl)-6H-furo[3,2-c]isoxazol-5-one A mixture of 1.5695 g (0.0069 mol) of the oxalate salt of S(−)-N-hydroxy-α-methylbenzenmethanamine, 0.7760 g (0.0050 mol) of trans-3-(dimethylamino)-2-propenoic acid-trans-propenyl ester and 65 ml of xylene was heated to reflux for a total of 55 min. under an inert atmosphere. The cooled mixture was filtered and washed with dichloromethane. Solvents were removed in vacuo and the product crystallized from diethyl ether. 0.4752 g (38%) of [3S-[1(S*),3β,3aβ,6aβ]]-tetrahydro-3-methyl-1-(1-phenylethyl)-6H-furo[3,2-c]isoxazol-5-one was obtained. An additional 0.2270 g (18%) of product was obtained by chromatography of the mother liquors on 250 g of silica gel eluting with diethyl ether/toluene (5:1 parts by volume). The analytical sample was recrystallized from diethylether. Mp 138°–138.5° C. $[\alpha]^{25}$ D+17.16 (c .6876, CHCl$_3$).

EXAMPLE 3

[4S-[4β,4(S*),5β,5(S*)]]Dihydro-5-(1-hydroxyethyl)-4-[(1-phenylethyl)amino]-2(3H)-furanone To a solution of 0.9892 g (0.004 mol) of 2aS-[2aα,5aα,6α,2(S*)] tetrahydro-6-methyl-(1-phenylethyl)-2Hfuro[3,2-c]isoxazol-4-(4H)-one and 120 ml of acetic acid/water (1:1 parts by volume) is added 3.7284 g of zinc dust. The mixture was stirred under an argon atmosphere for 22½ hours, then filtered, washing the residue with water then ethyl acetate. Solvents were removed in vacuo and the residue taken up in 400 ml of ethyl acetate. This solution was washed with 1×60 ml of 2 N potassium carbonate and dried over anhydrous sodium sulfate. Filtration and evaporation of solvent gave 0.9450 g of crude product. This was chromatographed on 20 g of silica gel, eluting with ethyl acetate to give 0.8913 g (89%) of [4S-[4β,4(S*),5β,5(S*)]]-dihydro-5-(1-hydroxyethyl)-4-[(1-phenylethyl)amino]-2(3H)-furanone as an oil. The analytical sample was recrystallized from diethyl ether. Mp 58°–60° C. $[\alpha]^{25}$ D−17.11° (c .9000, CH$_3$OH).

EXAMPLE 4

[4S-[4β,4(S*),5β,5(S*)]]-Tetrahydro-5-(1-hydroxyethyl)-2-oxo-N-(1-phenylethyl)furan-4-carbamic acid methyl ester To a solution of 10.0 g (0.04 mol) of [4S-[4β,4(S*),5β,5(S*)]]-dihydro-5-(1-hydroxyethyl)-4-[(1-phenylethyl)amino]-2(3H)-furanone in 400 ml of tetrahydrofuran is added 800 ml of 2 N sodium carbonate and 160 ml of methyl chloroformate. The mixture was stirred (with cooling) for 5 hours then extracted 4×500 ml of ethyl acetate. The combined ethyl acetate extracts were washed with water and dried over anhydrous sodium sulfate. The solvents were removed in vacuo, 12.9 g remained. This was chromatographed on 450 g of silica gel, eluting with ethyl acetate. 9.82 g of material was obtained which after crystallization from diethyl ether gave 6.94 g (54%) of [4S[4β,4(S*),5β,5(S*)]]-tetrahydro-5-(1-hydroxyethyl)-2-oxo-N-(1-phenylethyl)-furan-4-carbamic acid methyl ester. The analytical sample was recrystallized from ether, Mp 124.5° C. $[\alpha]^{25}$ D−82.10 (C 1.-378, CHCl$_3$).

EXAMPLE 5

[4S-[4β,4(S*),5β,5(S*)]]-Tetrahydro-5-(1-hydroxyethyl)-2-hydroxy-N-(1-phenylethyl)-furan-4-carbamic acid methyl ester Under an argon atmosphere of 3.07 g (0.010 mol) of [4S-[4β,4(S*),5β,5(S*)]]tetrahydro-5-(1-hydroxyethyl)-2-oxo-N-(1-phenylethyl)-furan-4-carbamic acid methyl ester in 300 ml of dry tetrahydrofuran was cooled with a dry ice/acetone bath and treated with 33 ml (ca. 0.050 mol) of diisobutylaluminumhydride in toluene (25%). After 5 hours, the excess hydride was quenched with methanol. 150 ml of saturated aqueous sodium sulfate was added followed by brine to break-up an emulsion. The mixture was extracted with 3×500 ml of methylene chloride. The organic extract was washed with water and dried over anhydrous sodium sulfate. Filtration and evaporation of solvent in vacuo gave 3.347 g of [4S-[4β,4(S*),5β,5(S*)]]-tetrahydro-5-(1-hydroxyethyl)-2-hydroxy-N-(1-phenylethyl)-furan-4-carbamic acid methyl ester as a residue which was used directly in the next step.

EXAMPLE 6

[2S-[2α,3β,4(S*),6β]]Tetrahydro-3-hydroxy-6-methoxy-2-methyl-4-N-(1-phenylethyl)-pyrancarbamic acid methyl ester The residue from example 5 (3.347 g, ca. 0.010 mol) was stirred with 5.75 g of Amberlite CG 120 (200–400 mesh) resin [a cationic sulfonated styrene divinyl benzene ion exchange resin] and 500 ml of methanol for 4 hours. The mixture was filtered and the solvent removed in vacuo. The residue was chromatographed on 150 g of silica gel eluting with hexane/ethyl acetate (1:1 by volume) to give 2.884 g (89%) of a mixture of anomers (ca 4:1 parts by weight). The major anomer [2S-

[2α,3β,4(S*),6β]]tetrahydro-3-hydroxy-6-methoxy-2-methyl-4-N-(1-phenylethyl)pyrancarbamic acid methyl ester was isolated by medium pressure liquid chromatography (hexane/ethyl acetate, 2:1 parts by volume). $[\alpha]^{25}$ D −106.10° (C 0.9020, CHCl$_3$).

EXAMPLE 7

[2S-(2α,3β,4α,6β)]-Tetrahydro-3-hydroxy-6-methoxy-2-methyl-2H-pyran-4-carbamic acid methyl ester A solution of 0.277 g (0.00086 mol) of [2S-[2α,3β,4(S*),6β]]-tetrahydro-3-hydroxy-6-methoxy-2-methyl-4-N-(1-phenylethyl)pyrancarbamic acid methyl ester in 3 ml of dry tetrahydrofuran was cooled to −78° C. and ca. 10 ml of dry ammonia distilled into the reaction flask (from sodium metal). Then ca. 0.10 g (0.004 mol) of sodium metal was added and the mixture stirred for 3 hours. Solid ammonium chloride was added, the cooling bath removed and ammonia evaporated over a slow stream of argon (overnight). The mixture was taken up in 20 ml of saturated aqueous sodium bicarbonate solution and extracted with 3×50 ml of methylene chloride. The combined methylene chloride extracts were dried over anhydrous sodium sulfate, filtered and the solvent removed in vacuo to give 0.171 g of crude product. This was crystallized from diethyl ether to give 0.142 g (75%) of [2S-(2α,3β,4α,6β)]-tetrahydro-3-hydroxy-6-methoxy-2-methyl-2H-pyran-4-carbamic acid methyl ester. The analytical sample was recrystallized from diethyl ether. Mp 142.5°–143° C. $[\alpha]^{25}$ D −162.64° (c .7071, CHCl$_3$).

EXAMPLE 8

Methyl 3-Amino-2,3,6-trideoxy-α-L-arabinohexopyranoside

A solution of 0.020 g (0.000091 mol) of [2S-(2α,3β,4α,6β)]-tetrahydro-3-hydroxy-6-methoxy-2-methyl-2H-pyran-4-carbamic acid methyl ester, 10 ml of water, 5 ml of methanol and 0.063 g of barium hydroxide octahydrate were heated to reflux under an inert atmosphere (argon) for 5 hours. An additional 0.12 g of barium hydroxide octahydrate was added and the mixture heated to reflux for 24 hours. Then, solid dry ice was added to the cooled mixture. The solution was filtered through diatomaceous earth, then solvents removed in vacuo. The residue was taken up in water and passed through AG-1-X4 (OH$^-$ form) ion exchange resin (a anionic polystyrene quaternary ammonium ion exchange resin). Solvents were removed in vacuo. The residue was sublimed using a distillation apparatus leaving 0.0080 g (54%) of methyl 3-amino-2,3,6-trideoxy-α-L-arabinohexopyranoside. Mp 129.5°–130.5° C. Lit.[1] mp. 132°–133° C. There was no melting point depression. NMR and mass spectra are identical to authentic material. $[\alpha]^{25}$ D = −140.38° (.2251, CH$_3$OH), Lit.[1] = −145.1° (.61, CH$_3$OH).
[1]S. K. Gupta Carbohydrate Res., 37, 38 (1974)

EXAMPLE 9

[2S(2α,3β,4α,6β)][Tetrahydro-6-methoxy-2-methyl-3-[(methylsulfonyl)oxy]-2H-pyran-4-yl]carbamic acid methyl ester To a solution of 0.3009 g (0.00137 mol) of [2S-(2α,3β,4α,6β)]-[tetrahydro-3-hydroxy-6-methoxy-2-methyl-2H-pyran-4-yl]carbamic acid methyl ester in 30 ml of dry pyridine cooled to 0° C. (ice bath) is added 0.6 ml (ca. 0.0078 mol) of methanesulfonylchloride. After 2½ hrs. ice was added. Five minutes later, 20 ml of saturated aqueous sodium bicarbonate solution was added and the mixture extracted 3×100 ml of methylene chloride. The combined extracts were dried over anhydrous sodium sulfate, filtered and solvents removed in vacuo to give 0.3635 g of crude product. This was recrystallized from diethyl ether to give 0.2800 g (69%) of [2S(2α,3β,4α,6β)][tetrahydro-6-methoxy-2-methyl-3-[(methylsulfonyl)oxy]-2H-pyran-4-yl]carbamic acid methyl ester first crop material. The analytical sample was recrystallized from ether. Mp 141°–142° C. $[\alpha]^{25}$ D = −109.50° (c .9717, CHCl$_3$).

EXAMPLE 10

[2S(2α,3α,4α,6β)]-(Tetrahydro-3-hydroxy-6-methoxy-2-methyl-2-H-pyran-4-yl)carbamic acid methyl ester A solution of 0.1189 g (0.0004 mole) [2S-(2α,3β,4α,6β)]-[tetrahydro-6-methoxy-2-methyl-3-[(methylsulfonyl)oxy]-2H-pyran-4-yl]carbamic acid methyl ester, 0.320 g of anhydrous sodium acetate and 40 ml of 65% dimethylformamide (aqueous) was heated (bath 105° C.) under an argon atmosphere for 42½ hours. The solvents were removed in vacuo. The residue was taken up in 20 ml of saturated aqueous sodium bicarbonate solution and extracted 3×60 ml of methylene chloride. The combined extracts were dried over anhydrous sodium sulfate, filtered and solvent removed in vacuo to give 0.081 g of crude product. This was chromatographed on 50 g of silica gel, eluting with ethyl acetate, 0.0435 g of [2S(2α,3α,4α,6β)]-(Tetrahydro-3-hydroxy-6-methoxy-2-methyl-2H-pyran-4-yl)carbamic acid methyl ester was obtained (50%). The analytical sample was recrystallized from diethyl ether/pentane, M.p. 90°–90.5° C.

EXAMPLE 11

Methyl-3-amino-2,3,6-trideoxy-α-L-lyxohexopyranoside

Under an argon atmosphere, 0.151 g (0.000069 mol) of [2S(2α,3α,4α,6β)]-tetrahydro-3-hydroxy-6-methoxy-2-methyl-2H-pyran-4-carbamic acid methyl ester. 0.10 g of Barium hydroxide octahydrate, 10 ml of water, and 5 ml of methanol were heated to reflux (bath at 110° C.) for 12 hrs, then allowed to stir overnight (ca. 8 hours). The solvents were removed in vacuo and the residue taken up in methanol and filtered. The solvent was removed in vacuo and this residue boiled 2×40 ml of diethyl ether, decanted and solvent removed to give 0.129 g of crude product. This material was passed through 2 ml of AG-1-X4 ion exchange resin (OH$^-$ form) with water as solvent. After evaporation of solvent, 0.0051 g of methyl-3-amino-2,3,6-trideoxy-α-L-lyxohexopyranoside remained (46%). This product was the same by nmr as authentic material. The product was sublimed at ca. 60° C. (0.05 mmHg). Mp 104°–106° C. which did not depress on mixture with authentic material (Literature[2] mp 109°–110° C.).
[2]J. P. Marsh, C. W. Mosher, E. M. Acton, and L. Goodman, Chem. Commun., 973(1967).

EXAMPLE 12

[3S-(3α,3aβ,6aβ1S*)]hexahydro-3-methyl-1-(1-phenylethyl)furo[3,2-c]isoxazol-5-ol To a solution of 3.711 g (0.015 mole) [3S-[1(S*),3β,3aβ,6aβ]]-tetrahydro-3-methyl-1-(1-phenylethyl)-6H-furo[3,2-c]isoxazol-5-one in 120 ml dry tetrahydrofuran at −78° C. (dry ice/acetone bath) was added 24 ml (ca. 0.036 mole) diisobutylaluminum hydride (25% solution in toluene) over ten minutes. The mixture was stirred under an argon atmosphere for 3 hr. Then 12 ml methanol was added to decompose excess hydride reagent and cooling bath was removed. After 15 minutes, 400 ml ethyl acetate was added and stirring continued for 30 min. The mixture was filtered through diatomaceous earth and solvent evaporated in vacuo to give 4.071 g crude product which was chromatographed on 250 g silica gel eluting with hexane/ethyl acetate (1:1 parts by volume) to give 3.67 g (98%) [3S-(3α,3aβ,-6aβ,1S*)]hexahydro-3-methyl-1-(1-phenylethyl)-furo[3,2-c]isoxazol-5-ol (2:1 parts by weight mixture at C5).

This was recrystallized from ether. mp 106°–108° C. NMR indicates the material to be a 65/35 parts by weight mixture of anomers. $[\alpha]_D = -37.61°$ (c, .9520, $CH_3OH$).

EXAMPLE 13

[3S-(3α,3aβ,6aβ,1S*)]-hexahydro-5-methoxy-3-methyl-1-(1-phenylethyl)furo[3,2-c]isoxazole A mixture of 7.36 g (0.030 mole) of [3S-(3α,3aβ,-6aβ,1S*()]hexahydro-3-methyl-1-(1-phenylethyl)-furo[3,2-c]isoxazol-5-ol (~2:1 mixture at C5) was used directly as crude material from Example 12. 415 ml methanol, 8.35 g Amberlite CG 120 200–400 mesh (H+ form) and 2.5 g 3A molecular sieves was stirred overnight, then filtered through diatomaceous earth. The filter cake was stirred 2 hr with 500 ml methanol and 15 ml triethylamine. This was filtered and both filtrates combined and solvents removed in vacuo to give 6.82 g (88%) crude product which was chromatographed on 250 g silica gel eluting with hexane/ethyl acetate (1:1 parts by volume). 6.337 g (82%) [3S-(3α,3aβ,6aβ,1S*)]-hexahydro-5-methoxy-3-methyl-1-(1-phenylethyl)-furo[3,2-c]isoxazole (a 3:1 parts by weight mixture) was obtained as a 3:1 mixture of anomers. This was distilled (bulb to bulb) 105° C. at 0.05 mmHg. $[\alpha]_D = -51.53°$ (c, 1.2692, $CH_3OH$).

EXAMPLE 14

[2S-(2β,2S*,3β)]-3-aminotetrahydro-5-methoxy-α-methyl-2-furanmethanol 10.58 g (0.040 mole) [3S-(3α,3aβ,6aβ,1S*)]hexahydro-5-methoxy-3-methyl-1-(1-phenylethyl)furo[3,2-c]-isoxazole (~3:1 parts by weight mixture at C5) was hydrogenated at 50 psi over 4.0 g 5% palladium on carbon catalyst in 930 ml methanol at room temperature over a weekend (ca. 46 hours). The mixture was filtered and solvents removed in vacuo to give 6.065 g crude product. The analytical sample of [2S-(2β,2S*,3β)]-3-aminotetrahydro-5-methoxy-α-methyl-2-furanmethanol was recrystallized from ether, mp 59°–62° C. $[\alpha]_D = -120.82°$ (c, .9982, $CH_3OH$). The $^{13}C$ NMR indicated only one anomer.

EXAMPLE 15

Methyl 3-amino-2,3,6-trideoxy-L-arabinohexopyranoside

A mixture of 4.524 g (0.028 mole) [2S-(2β,2S*,3β)]-3-aminotetrahydro-5-methoxymethyl-2-furanmethanol, 250 ml methanol, 2.57 g Amberlite CG 120 200–400 mesh (H+ form) and 1.5 g 3A molecular sieves was stirred for 20 hr. then 10 ml triethylamine was added. After 1 hour, the mixture was filtered through diatomaceous earth and filtrate evaporated in vacuo. The reaction was not complete (nmr) so the crude material was stirred with 250 ml methanol and 5.14 g Amberlite CG 120 200–400 mesh (H+ form) for 65 hr., then 15 ml triethylamine added. After stirring for 1½ hr, the mixture was filtered through diatomaceous earth. The filtercake was stirred 1 hour with 200 ml methanol, 5 ml triethylamine then filtered. The combined filtrates were concentrated in vacuo to give 4.056 g crude product from which 2.189 g methyl 3-amino-2,3,6-trideoxy-L-arabinohexopyranoside was crystallized from ether as a 2:1 parts by weight mixture (α:β) of anomers as determined by nmr.

EXAMPLE 16

Methyl 2,3,6-trideoxy-3-trifluoroacetamido-α-L-arabinohexopyranoside

A solution of 4 ml dry diethyl ether and 0.20 g (0.0012 mole) methyl-3-amino-2,3,6-trideoxy-L-arabinohexopyranoside (2:1 parts by weight mixture of anomers) from the previous example under an argon atmosphere was cooled with an ice bath. 0.8 ml trifluoracetic anhydride was added via syringe and the mixture stirred 15 minutes. The ice bath was removed and stirring continued for 3 hr. Solvent and excess reagent were removed in vacuo to produce methyl 2,3,6-trideoxy-3-trifluoroacetamido-4-O-trifluoroacetyl-α-L-arabinohexopyranoside. To this residue 6 ml methanol was added. After stirring at room temperature for 20 hours, the mixture was concentrated to dryness in vacuo. 0.344 g crude product remained. This was sublimed at 135° C. at 0.02 mmHg to give 0.279 g methyl-2,3,6-trideoxy-3-trifluoroacetamido-L-arabinohexopyranoside as a mixture of anomers. The anomers were separated by chromatography on silica gel (230–400 mesh) eluting with hexane/ethyl acetate (2:1 parts by volume).

Methyl-2,3,6-trideoxy-3-trifluoroacetamido-α-L-arabinohexopyranoside gave mp 192°–193.5° C. mixed mp. gave no depression $[\alpha]_D = -122°$ (c, 0.56,$CHCl_3$), $= -109°$ (c, 0.50, $CH_3OH$).

Methyl-2,3,6-trideoxy-3-trifluoroacetamido-β-L-arabinohexopyranoside gave mp 219.5°–221° C., $[\alpha]_D = +35°$ (C, 0.55, $CH_3OH$).

The beta-anomer was converted to a mixture of anomers by stirring with a cation exchange resin (sulfonated divinybenzenestyrene polymer) in methanol at room temperature, which was separated as described above.

EXAMPLE 17

Methyl-2,3,6-trideoxy-3-trifluoroacetamido-α-L-arabinohexopyranoside

To a solution of 0.161 g (0.001 mole) methyl-2,3,6-trideoxy-α-L-arabinohexopyranoside in 3 ml dry diethyl ether at 0° C. (ice bath for cooling) was added 0.231 g (0.0011 mole) trifluoroacetic anhydride. After 15 min. the cooling bath was removed. Stirring was continued for 3 hr. then the mixture was concentrated in vacuo. To the crude methyl-2,3,6-trideoxy-3-trifluoroacetamido-4-O-trifluoroacetyl-α-L-arabinohexopyranoside was added 6 ml dry methanol and the mixture stirred at room temperature for 20 hr. The mixture was concentrated in vacuo to give after recrystallization from acetone/hexane 0.195 g (76%) methyl-2,3,6-trideoxy-3-trifluoroacetamido-α-L-hexopyranoside. $[\alpha]_D = -123°$ (C, 0.55 $CHCl_3$) mp. 193°–195° C., mixed mp with authentic material gave no depression. Lit. $^3[\alpha]_D = -123°$ C. (C, 0.5, $CHCl_3$) mp. 195°–197° C.

[3]F. Arcamone et al., J. Med. Chem., 18, 703 (1975).

We claim:

1. A compound of the formula:

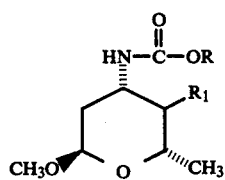

wherein R is lower alkyl; $R_1$ is ▬OR$_2$ or ///OH; and $R_2$ is hydrogen, phenylsulfonyloxy, lower alkyl-substituted phenylsulfonyloxy, or lower alkylsulfonyloxy or enantiomers or racemic mixtures thereof.

2. The compound of claim 1 wherein said compound is [2S(2α,3β,4α,6β)]-[tetrahydro-6-methoxy-2-methyl-3-[(methylsulfonyl)oxy]-2H-pyran-4-yl] carbamic acid methyl ester.

3. The compound of claim 1 wherein said compound is [2S(2α,3α,4α,6β)]-(tetrahydro-3-hydroxy-6-methoxy-2-methyl-2H-pyran-4-yl)carbamic acid methyl ester.

4. The compound of claim 1 wherein said compound is [2S-(2α,3β,4α,6β)]-tetrahydro-3-hydroxy-6-methoxy-2-methyl-2H-pyran-4-yl-carbamic acid methyl ester.

* * * * *